United States Patent [19]

Berenstein et al.

[11] Patent Number: 5,690,666
[45] Date of Patent: Nov. 25, 1997

[54] ULTRASOFT EMBOLISM COILS AND PROCESS FOR USING THEM

[75] Inventors: Alejandro Berenstein, New York, N.Y.; Ivan Sepetka, Redwood City, Calif.

[73] Assignee: Target Therapeutics, Inc., Fremont, Calif.

[21] Appl. No.: 978,320

[22] Filed: Nov. 18, 1992

[51] Int. Cl.$^6$ ............................................. A61M 29/00
[52] U.S. Cl. ........................................................ 606/191
[58] Field of Search ............................. 606/194, 191, 606/159, 151, 198; 604/159, 164; 128/772; 428/906, 371, 592; 623/1, 11, 12

[56] References Cited

U.S. PATENT DOCUMENTS

| | | |
|---|---|---|
| 1,341,052 | 5/1920 | Gale . |
| 1,667,730 | 1/1928 | Green .................................. 428/592 |
| 2,078,182 | 4/1937 | MacFarland ...................... 428/592 |
| 2,549,335 | 4/1951 | Rathus . |
| 3,649,224 | 3/1972 | Anderson et al. ................ 428/592 |
| 4,512,338 | 4/1985 | Balko et al. . |
| 4,638,803 | 1/1987 | Rand . |
| 4,820,298 | 4/1989 | Leveen et al. . |
| 4,850,960 | 7/1989 | Grayzel ............................. 606/194 |
| 4,954,126 | 9/1990 | Wallsten ............................ 606/191 |
| 4,957,501 | 9/1990 | Lahille et al. . |
| 4,994,069 | 2/1991 | Ritchart et al. . |
| 5,064,435 | 11/1991 | Porter . |
| 5,104,404 | 4/1992 | Wolff . |
| 5,108,407 | 4/1992 | Geremia et al. . |
| 5,122,136 | 6/1992 | Guglielmi et al. . |
| 5,133,731 | 7/1992 | Butler et al. . |
| 5,147,370 | 9/1992 | McNamara et al. ............... 606/194 |
| 5,151,105 | 9/1992 | Kwan-Gett ........................ 606/191 |
| 5,176,661 | 1/1993 | Evard et al. ...................... 606/194 |
| 5,186,992 | 2/1993 | Kite, III . |
| 5,203,772 | 4/1993 | Hammerslag et al. ............ 128/772 |
| 5,217,484 | 6/1993 | Marks . |

FOREIGN PATENT DOCUMENTS

| | | | |
|---|---|---|---|
| 592182 | 7/1925 | France | ................................. 606/191 |

*Primary Examiner*—Glenn Dawson
*Attorney, Agent, or Firm*—Morrison & Foerster LLP

[57] ABSTRACT

This invention is an exceptionally flexible, ultrasoft vaso-occlusive or embolism forming device. It is made of a radiopaque material which may be braided or coiled to form a long, thin threadlike device having little rigidity or column strength. The diameter of the device may be less than about 0.010 inches. The wire making up the device used to form the coil or braid is typically of a diameter less than about 0.002 inches. The device is sufficiently flexible and small that it may be hydraulically delivered to a site within the vasculature of the human body using an injected drug or fluid flush through a catheter. The device assumes a loose, random mass of threadlike material after being ejected from the catheter tip at the chosen vascular site. The device (whether coil or braid) may be used alone or in conjunction with larger coils or braids to achieve a denser occlusion or as a substrate to localize the subsequent infusion of tissue adhesives, particulate embolization devices, or chemotherapeutic agents in abnormal blood vessels and tissues or for the temporary occlusion of blood vessels during types of diminished blood flow testing. The invention also include processes for introducing the devices into the human body.

27 Claims, 4 Drawing Sheets

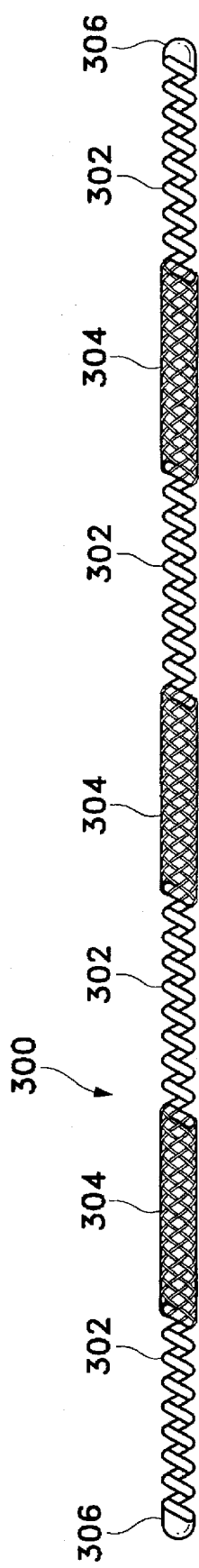
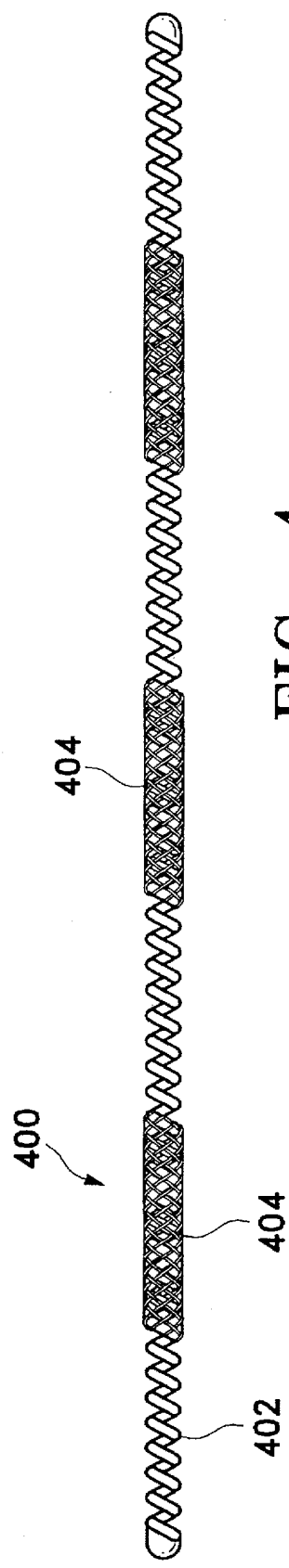
FIG. 3
FIG. 4

ULTRASOFT EMBOLISM COILS AND PROCESS FOR USING THEM

FIELD OF THE INVENTION

This invention is an exceptionally flexible, ultrasoft vaso-occlusive or embolism forming device. It is made of a radiopaque material which may be braided or coiled to form a long, thin threadlike device having little rigidity or column strength. The diameter of the device may be less than about 0.010 inches. The wire making up the device used to form the coil or braid is typically of a diameter less than about 0.002 inches. The device is sufficiently flexible and small that it may be hydraulically delivered to a site within the vasculature of the human body using an injected drug or fluid flush through a catheter. The device assumes a loose, random mass of threadlike material after being ejected from the catheter tip at the chosen vascular site. The device (whether coil or braid) may be used alone or in conjunction with larger coils or braids to achieve a denser occlusion or as a substrate to localize the subsequent infusion of tissue adhesives, particulate embolization devices, or chemotherapeutic agents in abnormal blood vessels and tissues. The device may be used for the temporary occlusion of blood vessels during types of diminished blood flow testing. The invention also include processes for introducing the devices into the human body.

BACKGROUND OF THE INVENTION

Endovascular therapy has been used in treating a variety of different conditions, including control of internal bleeding, occlusion of blood supply to tumors, and relief of vessel wall pressure in the region of aneurysm. A variety of different embolic agents are known as arguably suitable for such therapy.

One known embolic agent includes injectable fluids or suspensions, such as microfibrillar collagen, various polymeric beads, and polyvinyl alcohol foam. The polymeric agents may be additionally crosslinked, sometimes in vivo, to extend the persistence of the agent at the desired vascular site. These agents are often introduced into the vasculature through a catheter. After such introduction, materials there form a solid space-filling mass. Although they provide good short-term vaso-occlusion, they are ultimately reabsorbed in the process of vessel recanalization.

Polymer resins, typically cyanoacrylates, are also employed as injectable vaso-occlusive materials. The resins are typically mixed with a radio contrast material or made radiopaque by the addition of tantalum powder. Their use is fraught with problems in that placement of the mixture is quite difficult. Inadvertent embolisms in normal vasculature (due to the inability of controlling the destination of the pre-gelled resins) is not altogether uncommon. The material is also difficult or impossible to retrieve once it has been placed in the vasculature. Such resins have not been FDA approved, and a waiver must be requested in each instance where the materials are applied during human operative procedure.

A number of mechanical vaso-occlusive devices are widely used. One such device is a balloon which may be carried to the vessel site at the end of the catheter and there inflated with a suitable fluid, typically a polymerizable resin, and released from the end of the catheter. The balloon device has the advantage that it effectively fills the cross-section of the occluded vessel. However, when using intravascular balloon embolization of intracranial berry aneurysms, inflation of a balloon into the aneurysm carries some risk of aneurysm rupture due to possible "overfilling" of portions of the sac and due to the traction produced when detaching the balloon from the end of the catheter. Moreover, a vascular balloon is difficult to retrieve after the resin within the balloon sets up, and the balloon cannot be easily visualized using radiographic techniques unless it is filled with contrast material. Balloons have also been known to rupture during filling, or release prematurely during filling, or leak monomeric resin into the vasculature during the period before the monomer sets up into polymeric form.

Another type of mechanical vaso-occlusive device is a wire coil or braid which can be introduced through a catheter in stretched linear form and assumes an irregular shape upon discharge of the device from the end of the catheter. A variety of vaso-occlusive coils and braids are known. For instance, U.S. Pat. No. 4,994,069, to Richart et al., shows a flexible, preferably coiled, wire for use in small vessel vaso-occlusion. Unlike vaso-occlusive coils previously, Richart et al. teaches a coil which is fairly soft and is delivered to the site using a pusher within a catheter lumen. The Richart et al. coils are typically pushed into the desired vascular site in a linear configuration. Upon discharge from the catheter, the coil may undertake any of a number of random or regular configurations designed to fill the site. The coils are used for small vessel sites, e.g., 0.5–6 mm in diameter. The coils themselves are said to be between 0.010 and 0.030 inches in diameter. The length of the coiled wire is typically 15–20 times the diameter of the vessel to be occluded. The wire used to make up the coils may be 0.002 to 0.006 inches in diameter. Tungsten, platinum, and gold threads or wires are said to be preferred. These coils have a variety of benefits, including the fact that they are relatively permanent, they can be easily imaged radiographically, they may be located at a well-defined vessel site, and they can be retrieved.

A variation of the mechanical endovascular coil is found in U.S. Pat. No. 5,122,132, to Guglielmi et al. Guglielmi's coils are typically used in intracranial aneurysms because of their effectiveness in quickly forming controlled emboli. The disclosed coils are similar to those of Richart et al. in size and in composition. However, the method of introducing the coil to the vascular site is somewhat different. Rather than mechanically thrusting the coil into the chosen site, the coil is placed at the site and a small voltage is applied to the guidewire supporting the coil so that the coil is electrolytically detached from the distal tip of the guidewire. The step of electrolytically detaching the coil has the added benefit of forming a thrombus as the coil is detached. Again, as noted above, the Guglielmi coils may be stainless steel or platinum or the like, and are typically 0.010 to 0.020 inches in diameter and are made using wire having approximate diameters of 0.001 to 0.005 inches. The coils in this service are typically between 1 and 50 centimeters in length.

None of this background shows coils or braids having diameters less than about 0.01 inches in diameter, nor their placement by fluid delivery through catheter.

SUMMARY OF THE INVENTION

This invention is an exceptionally flexible, ultrasoft vaso-occlusive or embolism device. It is made of a radiopaque material which may be braided or coiled to form a long, thin threadlike device having little rigidity or column strength. The diameter of the device may be less than about 0.010 inches, preferably less than about 0.0075 inches in diameter. The wire making up the device is typically of a diameter less than about 0.002 inches. The device is sufficiently flexible and small that it may be hydraulically delivered to a site within the vasculature of the human body using a catheter. The device is so light that it typically cannot be pushed from the catheter in the way that coils are often introduced into vascular sites. Because of their flexibility and size, there is little opportunity for friction to develop with the catheter lumen.

These devices may be used with guide wire—directed catheters and with flow directed catheters, even those which are very light in their distal regions. This coil provides opportunities for placement of coils in vascular regions otherwise not routinely accessible due to their remote nature.

The device typically assumes a loose, random mass after being ejected from the catheter tip at the selected vascular site. The device, whether coil or braid, may be used in conjunction with larger coils or braids to achieve a denser occlusion or as a substrate to localize the subsequent infusion of tissue adhesives, particulate embolization devices, or chemotherapeutic agents in abnormal blood vessels and tissues, or for the temporary occlusion of blood vessels during types of diminished blood flow testing. The invention also include processes for introducing the devices into the human body.

This invention is also a method for first introducing a larger vaso-occlusive coil to the vascular site desired by the attending physician, followed by the introduction of the inventive coil so as to fill the interstices left by the larger coils and thereby form a denser occlusion. The devices may also be introduced by themselves, if so desired.

BRIEF DESCRIPTION OF THE DRAWINGS

FIG. 3 shows an enlarged side view of a combination coil and braid made according to this invention.

FIG. 4 is a close-up drawing of a variation of the FIG. 3 device in which a braided material is woven on the outside of the coil.

DESCRIPTION OF THE INVENTION

Figure 1:
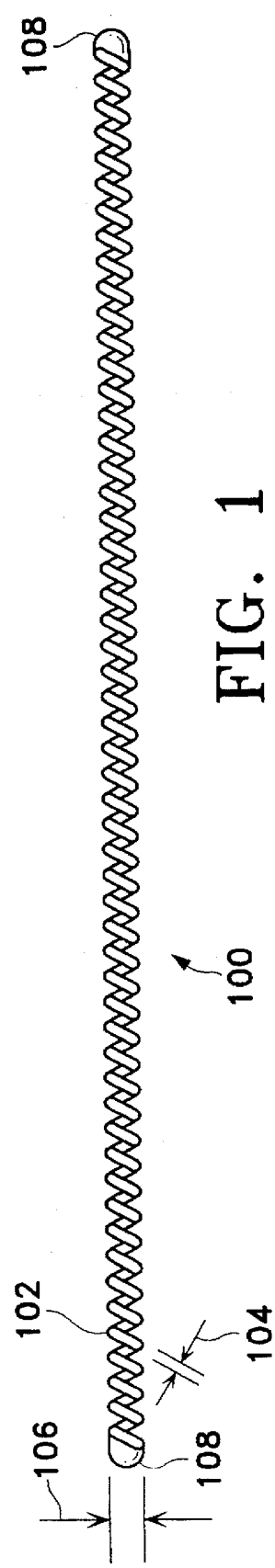
FIG. 1 shows an enlarged side view of a coil made according to this invention.

FIG. 1 shows a coil (100) made according to this invention. It is a fairly straightforward device typically formed by wrapping or winding a fine wire (102), preferably having a diameter (104) of 0.00075 to about 0.00225 inches, more preferably about 0.001 to 0.002 inches, about a spinning mandrel using well-known coil-manufacturing techniques. A separate end cap (108) or termination piece may be included at the end of the coil. The terminator (108) may be a separate piece or a fused portion of the coil or a bit of a filled material such as an epoxy. The major function of the end piece is to prevent the coil from catching on the interior of the catheter lumen or vessel.

In producing the coil, the coil-manufacturing method is adjusted to produce a single-layer coil typically with a minimum helical pitch, that is to say, the windings are fairly closely packed. Typically, the mandrel will be of such a diameter that the outside coil diameter (106) will be less than 0.010 inches, preferably between 0.004 and 0.095 inches, and most preferably between 0.004 and 0.075 inches. The soft, flexible coil thus produced is cut to desired lengths after removal from the mandrel. We have found that the device is especially suitable for the noted service when the device (coil, braid, or combination) deflects more than about 20° (preferably more than about 35°) under its own weight over the first centimeter of length, when supported at a single end. The length of the coil may be between 2 mm and 120 cm, typically between 30 cm and 120 cm.

Instead of the wire shown in FIG. 1, the coil may be produced from a ribbon whose major axis is between 0.001 and 0.002 inches and whose minor axis is 0.0005 and 0.001 inches. Coils produced from ribbons are often moderately stiffer than those produced from wire. Smaller diameter coils are often more readily produced.

The regularity of winding shown in FIG. 1 is not mandatory; the windings may be irregular or of varying pitch. The coil (100) shown in FIG. 1 (and the variations of the invention which are described below) may be produced from any of a number of different materials. The material must be radiopaque so that the coil and its position may be readily monitored within the human vasculature. Suitable materials include biocompatible metals, polymers, and alloys. For instance, biocompatible, radiopaque metals include silver, gold, palladium, platinum, tungsten, iridium, and various stainless steels. Other alloys such as platinum and tungsten (preferably 92% platinum and 8% tungsten) are suitable and, indeed, are often most preferred. The platinum-tungsten alloys desirably have a tensile strength of at least about 180 kpsi and, for a wire of a nominal 0.001" diameter, have a reaking load of 0.17 lb with a minimum elongtion of 2% measured at a speed of 1.0 in/min. Various biocompatible polymers including polyethylene, polyurethane, polypropylene, and the like are suitable for use in these devices, but, because of their lack of radiopacity, must usually be teamed with a radiopaque marker to allow proper positioning of the coil within the body. Similarly, other inorganic materials such as fibrous carbon are suitable and may be used in the invention.

After formation of the coil, its interior may be filled with a drug material such as a drug concentrate and its ends partially sealed for slow drug release from the coil in an in vivo aqueous environment. The ends of the coil may be sealed by a water-soluble plug for storage, if so desired.

Figure 2:
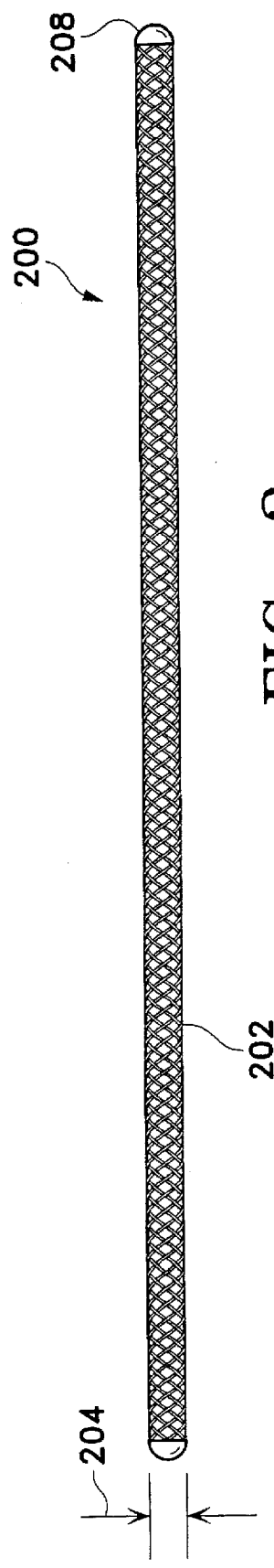
FIG. 2 shows an enlarged side view of a braid made according to this invention.

FIG. 2 shows a braided (or otherwise) woven vaso-occlusive device (200) made according to the invention. The braided occlusive device (200) is tubular and produced by weaving fibers or wires (202) over a mandrel much in the same way the coil of FIG. 1 was made. Woven braids of this size are not common but are made according to known techniques. The wire or fibers (202) in this variation of the invention may be any of the radiopaque or polymeric materials noted above, and additionally the braid may be made of a combination of those materials either alone or in combination with other suitable polymeric or filamentary materials such as DACRON, cotton, or other materials. Organic fibers such as DACRON or cotton provide a ready substrate for clot formation in the interior region of a vessel. Often the radiopaque portion of the coil provides only a way to anchor the coil onto the vessel wall at the site of release.

The FIG. 2 braid or woven device (200) is of a diameter (204) similar to the coil (106) in FIG. 1. The (106) braid may have a termination piece or section (208) similar in constitution to the analogous portion shown in FIG. 1 above. The length of the braid may similarly be 2 mm to 120 cm.

FIG. 3 shows a side view of a combination coil/braid vaso-occlusive device (300) according to the invention. This combination (300) is a sequence of coils (302) and braids (304) similar in make-up and size as the devices shown in FIGS. 1 and 2. Lengths of various coils (302) and braids (304), each often 2 mm to 20 cm in length, are joined together at their respective ends to form the combination device. The overall length of the device, as with those above, may be 2 mm to 120 cm. The device may also have caps or termination pieces (306) on the ends of the device.

FIG. 4 shows another variation of a coil/braid combination (400). In this variation, however, as is shown by the cutaway insert, the substrate coil is identical to the coil shown in FIG. 1 herein. The braid (404) is woven on the exterior of the coil. In this instance, the braid is more desirably a fibrous material such as DACRON or cotton. The braid may, however, be a radiopaque material such as the metals and alloys and polymers discussed above. The braid may be joined by welding, melting, or by adhesion to the underlying coil (402).

Each of the variations discussed above, when provided in the proper size range and materials, is an extremely soft and flexible device, whether the device be coil or braid. These devices exert little if any radial force on the blood vessels into which they are placed. They are sufficiently flexible and small that they may be carried by blood flow after ejection from the distal tip of the catheter by which they are introduced to a narrowing region in the vascular lumen where the coil wedges or rolls upon itself and wedges within the blood vessel. The fluidlike properties of the coil enable it to conform to the complex geometry of certain fragile, abnormal blood vessels, and in so doing, minimize the risk of causing trauma to or even perforation of those blood vessels. Such flow properties also enable coil placement in vasculature currently unreachable by catheterization, such as those within an arteriovenous malformation (AVM).

Although the device is very flexible in all of its configurations, it may be produced having a modest amount of "preform". Such a treatment will provide some additional randomness when the coil is placed at its site within the vasculature.

Figure 5:
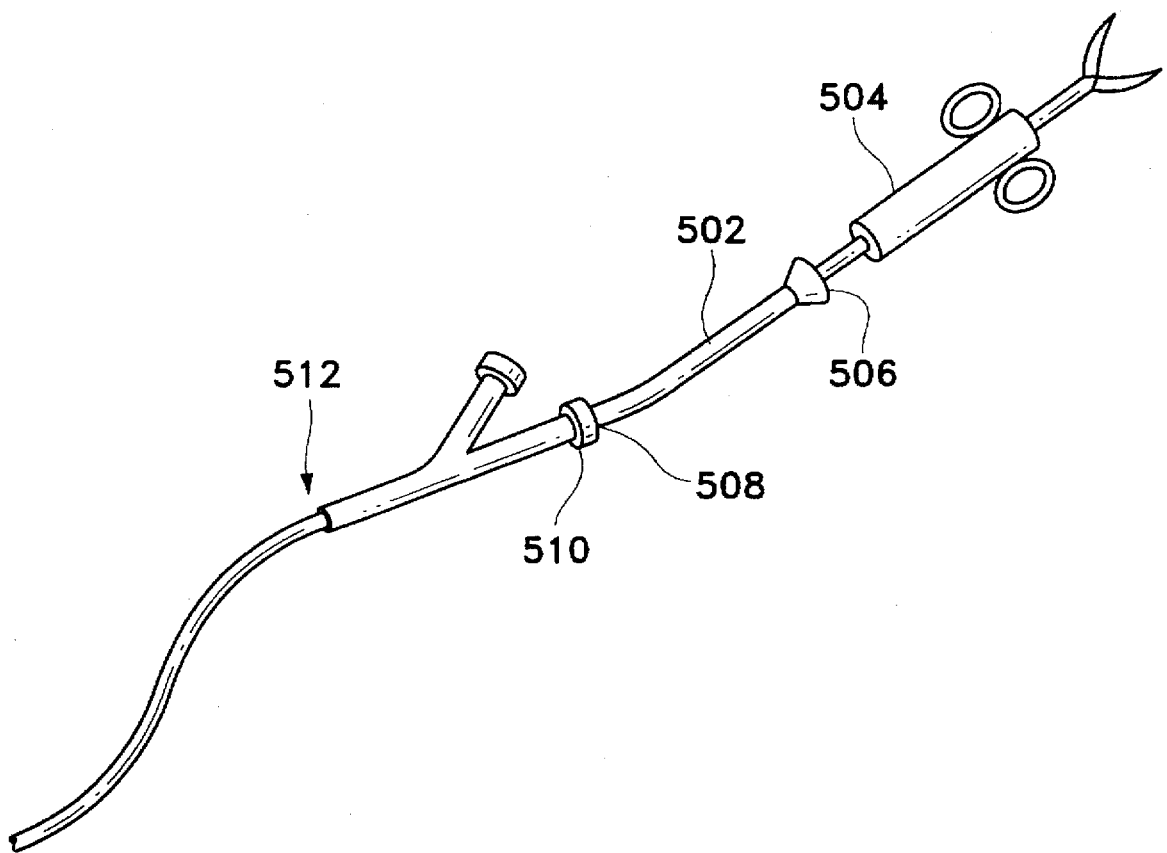
FIG. 5 is a clinical set-up which may be used to introduce the coils into the vasculature.

FIG. 5 shows a setup for delivering the coils of this invention to a vascular site. In this instance, the coils are held in an introducer sheath (502) and delivered through a catheter (512) to the desired site motivated by a syringe (504), containing a suitable fluid. The proximal end (506) of the introducer sheath (502) is connected to the fluid-containing syringe. The distal end (508) of the introducer sheath (502) is introduced to the catheter hub (510). The lumen in catheter assembly (512) has been previously cleared of guidewires and other interior constrictions. The plunger on syringe (504) is simply pushed down, and the device within introducer sheath (502) is carried down through catheter (512) to the injection site. After the device is injected to the desired site, additional devices may be injected by swapping another introducer sheath (502) with its related device.

This procedure may be carried out after the catheter has been used to introduce coils of larger size to a particular site. The later introduction of the devices of this invention will enhance the thrombolytic potential of the earlier-introduced coil in that the inventive devices will tend to fill the interstices left by the larger coils and achieve a more densely packed occlusion site.

Additionally, this process may include the step of introducing polymer resins, such as cyanoacrylate resins (particularly n-butylcyanoacrylate) to the intended site after the inventive coils or braids are in place. Said another way, the inventive coils or braids form a substrate for these tissue adhesives, or particulate embolization materials such as microparticles of polyvinyl alcohol foam, or various chemotherapeutic agents. The catheters suitable for use in introducing these devices are discussed in significant detail in U.S. Pat. No. 4,994,069, to Richart et al., as was discussed above.

EXAMPLE

This example demonstrates the significant difference between a preferred embodiment of this inventive coil and similar commercial coils of the type discussed in Richart et al. The example shows how much more flexible is the inventive coil than the other coils.

Three coils were measured. Coil A was a coil made according to the invention. Coils B and C are commercially avalable from Target Therapeutics Incorporated for a variety of uses. The coils' physical descriptions are as follows.

TABLE I

| COIL | COIL O.D. | WIRE Dia. | PITCH |
| --- | --- | --- | --- |
| A | 0.007" | 0.001" | 0.001" |
| B1 | 0.010" | 0.002" | 0.002" |
| B2 | 0.010" | 0.002" | 0.002+"* |
| C | 0.015" | 0.003" | 0.003" |

*(physically stretched before measuring)

An introducer, a tapered length of tubing having an inside diameter of 0.010 inches, was taped to an angle template taken from an optical comparator. The respective coils were placed within the introducer and allowed to extend from the tip of the introducer at various lengths. The coils were extended to 1.0 cm and beyond. The introducer was held level and the angle between the tip of the introducer and the end of the coil was measured as a function of the length of the coil extending from the introducer. The results of the tests are shown in Table II below and in FIG. 6.

TABLE II

| COIL → extension (mm) ⇓ | A (°) | B1 (°) | B2 (°) | C (°) |
| --- | --- | --- | --- | --- |
| 1 | 0.75 | 0 | 0 | — |
| 2 | 4.0 | 2 | 0 | — |
| 3 | 5.5 | 2 | 0 | — |
| 4 | 10.0 | 2 | 0 | — |
| 5 | 18.5 | 2 | 1 | — |
| 6 | 24.5 | 2 | 2 | — |
| 7 | 33.5 | 2 | 3.5 | — |
| 8 | 42.5 | 3 | 4 | — |
| 9 | 45 | 3 | 7 | — |
| 10 | 51 | 3 | 13 | — |
| 20 | 69 | 20 | — | 26.5 |
| 30 | 80 | 51 | — | 47 |
| 40 | 84 | 65 | — | — |
| 50 | 88 | 73 | — | 72 |

The depicted data for the inventive Coil A and the Coil C are averages of a number of measurements of similar coils.

Figure 6:
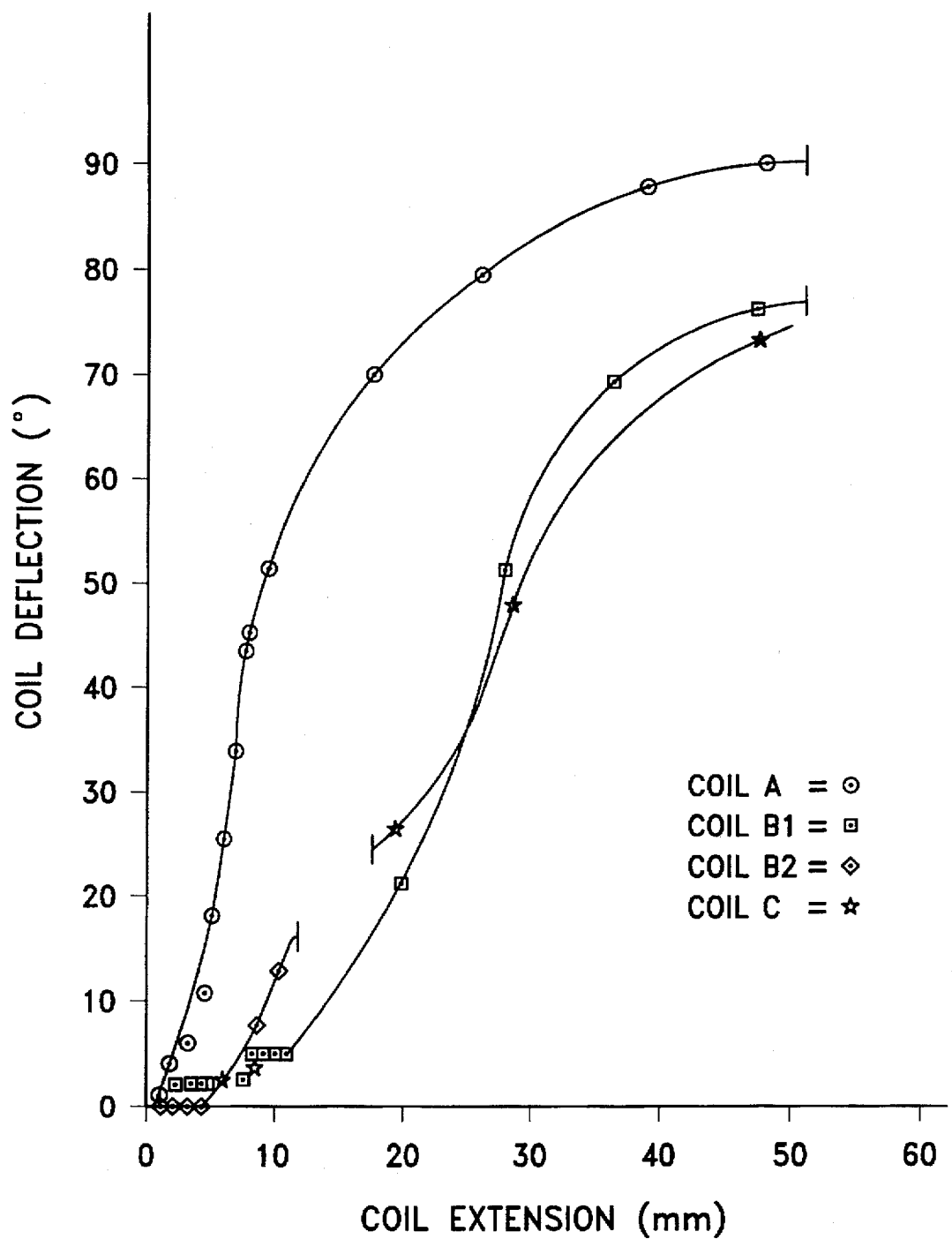
FIG. 6 is a graph comparing deflection versus extension for three coils; one coil made according to this invention and two commercially available embolism coils made generally according to the prior art.

The relationship between the extension of the coils and their resulting deflection in degrees is shown in FIG. 6. It is readily observed that, at a 10 mm extension, the angle of deflection for the inventive coil is about 50°. For the other coils, the deflection is typically only about 10% of that value. Consequently, it may be understood that the bending radius of the inventive coil is much smaller, the force needed to bend the coil is significantly smaller, and consequently the coil will move through tortuous pathways both in the vasculature and in the catheter with significantly more ease than would be observed by the other coils.

Many alterations and modifications may be made by those of ordinary skill in the art without departing from the spirit and scope of the invention. The illustrated embodiments have been shown only for purposes of clarity and examples, and should not be taken as limiting the invention as defined by the following claims, which include all equivalents, whether now or later devised.

We claim as our invention:

1. A flexible, vaso-occlusive device comprising a radiopaque coil having an outside diameter less than about 0.010 inches which is sufficiently flexible that a 1 cm length of coil supported horizontally at one end will deflect more than 20° under its own weight.

2. The device of claim 1, wherein the material of the coil comprises silver, gold, palladium, platinum, tungsten, iridium, stainless steel, or alloys thereof.

3. The device of claim 2 wherein the radiopaque material comprises an alloy of platinum and tungsten.

4. The device of claim 1 wherein the coil is regularly wound.

5. The device of claim 1 wherein the coil is not regularly wound.

6. The device of claim 1 wherein the outside diameter is between 0.004 inches but less than about 0.0095 inches.

7. The device of claim 6 wherein the outside diameter is between 0.004 and 0.0075 inches.

8. The device of claim 1 wherein the coil comprises wire having a diameter of between 0.00075 and less than 0.00225 inches.

9. The device of claim 8 wherein the coil comprises wire having a diameter of between 0.001 and 0.002 inches.

10. The device of claim 8 wherein the coil comprises wire having a diameter of about 0.001 inches.

11. The device of claim 1 wherein the device is sufficiently flexible that a 1 cm length of coil supported horizontally at one end will deflect more than 35° under its own weight.

12. The device of claim 1 wherein the length of the device is between 2 mm and 120 cm.

13. The device of claim 12 wherein the length of the device is between 30 cm and 120 cm.

14. A flexible, vaso-occlusive device comprising a coil which is sufficiently flexible that a 1 cm length of coil supported horizontally at one end will deflect more than 20° under its own weight.

15. The device of claim 14, wherein the material of the coil comprises silver, gold, platinum, palladium, tungsten, iridium, stainless steel, or alloys thereof.

16. The device of claim 15 wherein the device comprises an alloy of platinum and tungsten.

17. The device of claim 14 wherein the coil is regularly wound.

18. The device of claim 14 wherein the coil is not regularly wound.

19. The device of claim 14 wherein the coil comprises wire having a diameter of between 0.00075 and 0.00225 inches.

20. The device of claim 19 wherein the coil comprises wire having a diameter of between 0.001 and 0.002 inches.

21. The device of claim 20 wherein the coil comprises wire having a diameter of about 0.001 inches.

22. The device of claim 14 wherein the coil comprises a ribbon having a major axis between 0.001 and 0.002 inches and a minor axis between 0.0005 and 0.001 inches.

23. The device of claim 14 wherein the device is sufficiently flexible that a 1 cm length of the device supported horizontally at one end will deflect more than 35° under its own weight.

24. The device of claim 14 wherein the length of the device is between 2 mm and 120 cm.

25. The device of claim 24 wherein the length of the device is between 30 cm and 120 cm.

26. A flexible, vasoocclusive device having an outside diameter less than about 0.010 inches which is sufficiently flexible that a 1 cm length of said device supported horizontally at one end will deflect more than 20° under its own weight.

27. The device of claim 26, wherein the device is selected from radiopaque coils, radiopaque braids, sequences of coils and braids joined at their respective ends, or coils having tubular braids woven on their exterior surfaces.

* * * * *

UNITED STATES PATENT AND TRADEMARK OFFICE

CERTIFICATE OF CORRECTION

PATENT NO. : 5,690,666

DATED : November 25, 1997

INVENTOR(S) : Berenstein et al.

It is certified that error appears in the above-identified patent and that said Letters Patent is hereby corrected as shown below:

*Column 4, line 33*: please change "1B" to -- lb --.

*Column 4, line 64*: please insert "diameter" after -- coil --.

*Column 4, line 64*: please delete "(106)" before -- braid --.

Signed and Sealed this

Third Day of February, 1998

Attest:

BRUCE LEHMAN

*Attesting Officer*　　　*Commissioner of Patents and Trademarks*